(12) United States Patent
Liu (10) Patent No.: US 10,973,689 B2
(45) Date of Patent: Apr. 13, 2021

(54) SNOW GOGGLE DEVICE

(71) Applicant: ASWAN INTERNATIONAL CORP., Taipei (TW)

(72) Inventor: Wei-Ting Liu, Taipei (TW)

(73) Assignee: ASWAN INTERNATIONAL CORP., Taipei (TW)

( * ) Notice: Subject to any disclaimer, the term of this patent is extended or adjusted under 35 U.S.C. 154(b) by 303 days.

(21) Appl. No.: 16/132,550

(22) Filed: Sep. 17, 2018

(65) Prior Publication Data
US 2020/0085623 A1 Mar. 19, 2020

(51) Int. Cl.
*A61F 9/02* (2006.01)

(52) U.S. Cl.
CPC .............. *A61F 9/025* (2013.01); *A61F 9/029* (2013.01)

(58) Field of Classification Search
CPC .. A61F 9/027; A61F 9/02; A61F 9/025; A61F 9/029; B63C 2011/128; A44B 11/2553
USPC ...................................................... 2/448, 452
See application file for complete search history.

(56) References Cited

U.S. PATENT DOCUMENTS

| | | | | |
|---|---|---|---|---|
| 4,843,655 A * | 7/1989 | Hegendorfer | ............ | A61F 9/025 2/449 |
| 5,357,292 A * | 10/1994 | Wiedner | ................ | A61F 9/025 2/450 |
| 5,652,954 A * | 8/1997 | Paiement | ................ | A61F 9/027 2/10 |
| 5,870,165 A * | 2/1999 | Wang | ........................ | G02C 1/02 351/110 |
| 5,909,267 A * | 6/1999 | Hall | ........................ | A61F 9/028 2/453 |
| 6,009,564 A * | 1/2000 | Tackles | ...................... | A61F 9/02 2/436 |
| 6,024,446 A * | 2/2000 | Hall | ........................ | A61F 9/025 2/448 |
| 6,477,717 B1 * | 11/2002 | Winefordner | ........... | B63C 11/12 2/428 |
| 8,668,330 B2 * | 3/2014 | Reyes | ...................... | G02C 1/04 351/106 |
| 8,746,877 B2 * | 6/2014 | Belbey | ..................... | F41H 1/02 351/156 |
| 2009/0038059 A1 * | 2/2009 | McNeal | ................. | G02C 5/001 2/439 |

(Continued)

*Primary Examiner* — Sally Haden
(74) *Attorney, Agent, or Firm* — Li & Cai Intellectual Property (USA) Office (57) ABSTRACT

A snow goggle device includes a spectacle frame, two pivoting members movably connected to the spectacle frame, and a curved lens pivotally connected to the two pivoting members. Each pivoting member is cooperated with the spectacle frame to form with a first segment movable along a straight path and a second segment movable along an arced path, and includes a third segment synchronously movable with the first segment and the second segment. When the first and the second segments of each pivoting member are synchronously moved, the third segments drive the curved lens to move with respect to the spectacle frame between a closed position and an open position, synchronously causing a deformation of the curved lens. When the curved lens is at the closed position or the open position, the curved lens receives a stress that is smaller than a stress generated from the deformation.

10 Claims, 13 Drawing Sheets

(56) References Cited

U.S. PATENT DOCUMENTS

2013/0185849 A1* 7/2013 Laughlin ................ A61F 9/025
2/431

* cited by examiner

SNOW GOGGLE DEVICE

FIELD OF THE DISCLOSURE

The present disclosure relates to a snow goggle device, and more particularly to a snow goggle device having a curved lens that is movable.

BACKGROUND OF THE DISCLOSURE

A conventional snow goggle includes a spectacle frame and a lens fastened to the spectacle frame. The conventional snow goggle can be provided with a pivotal member to connect the spectacle frame and the lens, so that the lens can be rotated with respect to the spectacle frame by the pivoting member.

However, in rotation of the lens of the conventional snow goggle, a portion of the lens connected to the pivoting member is rotated along a circular path by taking a portion of the spectacle frame connected to the pivoting member as a fulcrum (or a rotating axis). Since the portion of the spectacle frame connected to the pivoting member is not moved during rotation, the circular path is limited to having a small radius based on the size of the spectacle frame, so that the lens of the conventional snow goggle sustains a large deformation and generates a large stress when being rotated, which are also sustained by the spectacle frame and the pivoting member.

SUMMARY OF THE DISCLOSURE

In response to the above-referenced technical inadequacies, the present disclosure provides a snow goggle device to effectively improve the issues associated with conventional snow goggles.

In one aspect, the present disclosure provides a snow goggle device, which includes a spectacle, two pivoting members, and a curved lens. The spectacle frame surroundingly defines an accommodating space. The spectacle frame includes two carrying portions arranged at two opposite sides of the accommodating space. The two pivoting members each have a matching portion. The two matching portions are respectively and movably connected to the two carrying portions, and are substantially in a mirror symmetrical arrangement. Each of the two matching portions and the corresponding carrying portion are co-defined as a pivoting module. In each of the two pivoting modules, the matching portion is cooperated with the carrying portion to form with a first segment movable along a straight path and a second segment movable along an arced path, and the matching portion includes a third segment synchronously movable with the first segment and the second segment. The arced path is located in an extension direction of the straight path. The curved lens is pivotally connected to the third segment of each of the two pivoting modules. When the first segment and the second segment of each of the two pivoting modules are synchronously moved, the third segments of the two pivoting members drive the curved lens to move with respect to the spectacle frame between a closed position and an open position, synchronously causing a deformation of the curved lens. When the curved lens is at the closed position, the curved lens is disposed on the spectacle frame to enclose one side of the accommodating space and receives a first stress. When the curved lens is at the open position, the curved lens is spaced apart from the spectacle frame and receives a second stress. When the curved lens is moved between the closed position and the open position, the curved lens receives a third stress that is generated from the deformation and that is larger than each of the first stress and the second stress.

In one aspect, the present disclosure provides a snow goggle device, which includes a spectacle frame, two pivoting members, and a curved lens. The spectacle frame surroundingly defines an accommodating space. The spectacle frame includes two carrying portions arranged at two opposite sides of the accommodating space, and each of the two carrying portions includes a straight groove and an arced groove. The two pivoting members are respectively and movably connected to the two carrying portions, and are substantially in a mirror symmetrical arrangement. Each of the two pivoting members includes a L-shaped frame, a first pivot connected to an end of the L-shaped frame, a second pivot connected to a corner of the L-shaped frame, and a third pivot connected to the other end of the L-shaped frame. In each of the two pivoting members and the corresponding carrying portion, an inner edge of the corner of the L-shaped frame has an angle within in a range of 85-105 degrees, the first pivot is movably inserted into the straight groove, and the second pivot is movably inserted into the arced groove. The curved lens is pivotally connected to the third pivot of each of the two pivoting members. When the first pivot and the second pivot of each of the two pivoting member are synchronously moved along the straight groove and the arced groove, the third pivots of the two pivoting members drive the curved lens to move with respect to the spectacle frame between a closed position and an open position, synchronously causing a deformation of the curved lens. When the curved lens is at the closed position, the curved lens is disposed on the spectacle frame to enclose one side of the accommodating space and receives a first stress. When the curved lens is at the open position, the curved lens is spaced apart from the spectacle frame and receives a second stress. When the curved lens is moved between the closed position and the open position, the curved lens receives a third stress that is generated from the deformation and that is larger than each of the first stress and the second stress.

Therefore, in the snow goggle device of the present disclosure, the structural cooperation between the spectacle frame and each of the pivoting members (e.g., the first segment and the second segment of each of the pivoting members are moved along the straight path and the curved path) can be provided to enlarge a radius of a moving path that is related to part of the curved lens pivotally connected to the third segment of the pivoting member, so that the deformation of the curved lens can be effectively reduced.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The present disclosure will become more fully understood from the detailed description and the accompanying drawings, in which.

DETAILED DESCRIPTION OF THE EXEMPLARY EMBODIMENTS

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

Figure 1:
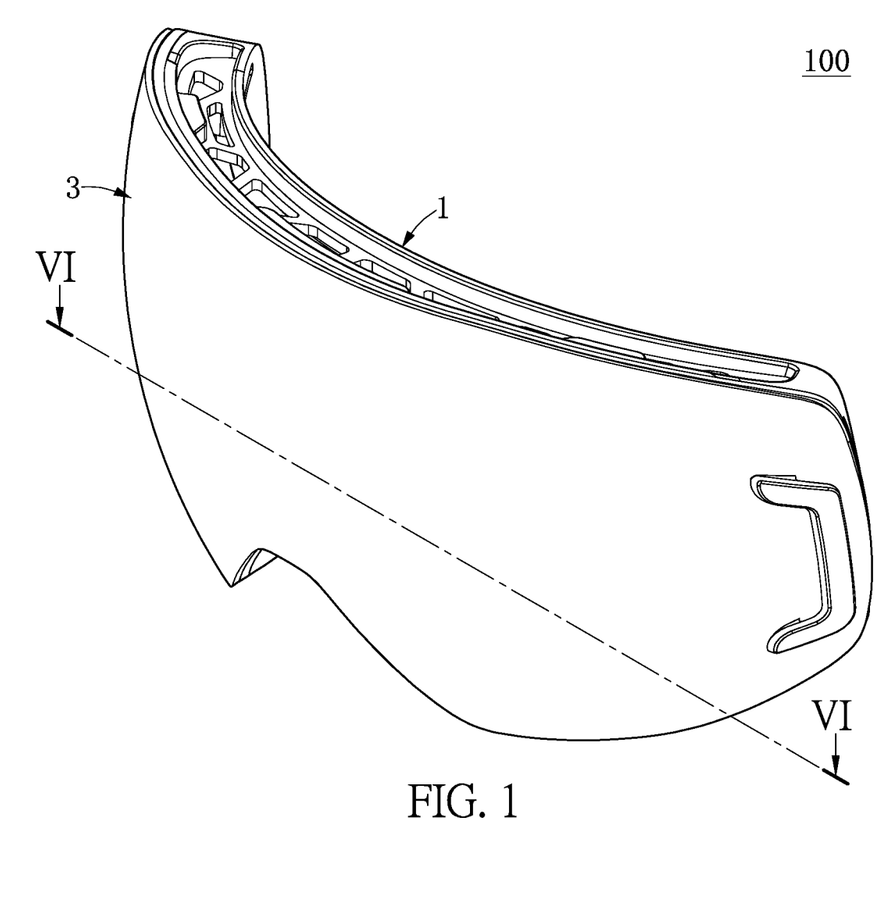
FIG. 1 is a perspective view of a snow goggle device that is at a closed position according to an embodiment of the present disclosure.
Figure 2:
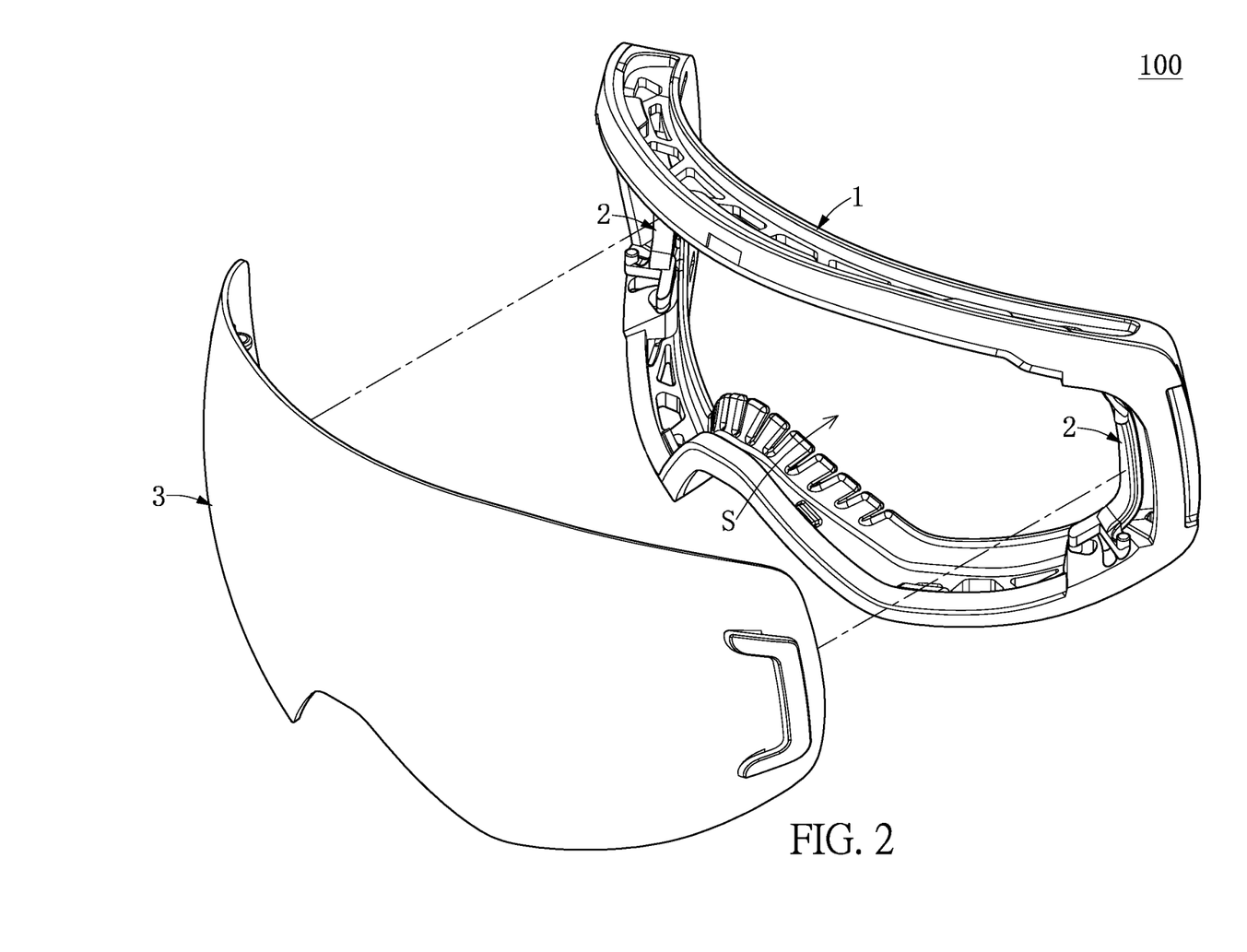
FIG. 2 is an exploded view of FIG. 1.

Referring to FIG. 1 to FIG. 14, an embodiment of the present disclosure provides a snow goggle device 100 for being worn on (e.g., being gaplessly attached with) a user's face so as to protect the user's eyes. As shown in FIG. 1 and FIG. 2, the snow goggle device 100 includes a spectacle frame 1, two pivoting members 2 movably connected to the spectacle frame 1, and a curved lens 3 pivotally connected to the two pivoting members 2. The following description discloses the structure and connection relationship of each component of the snow goggle device 100.

Figure 3:
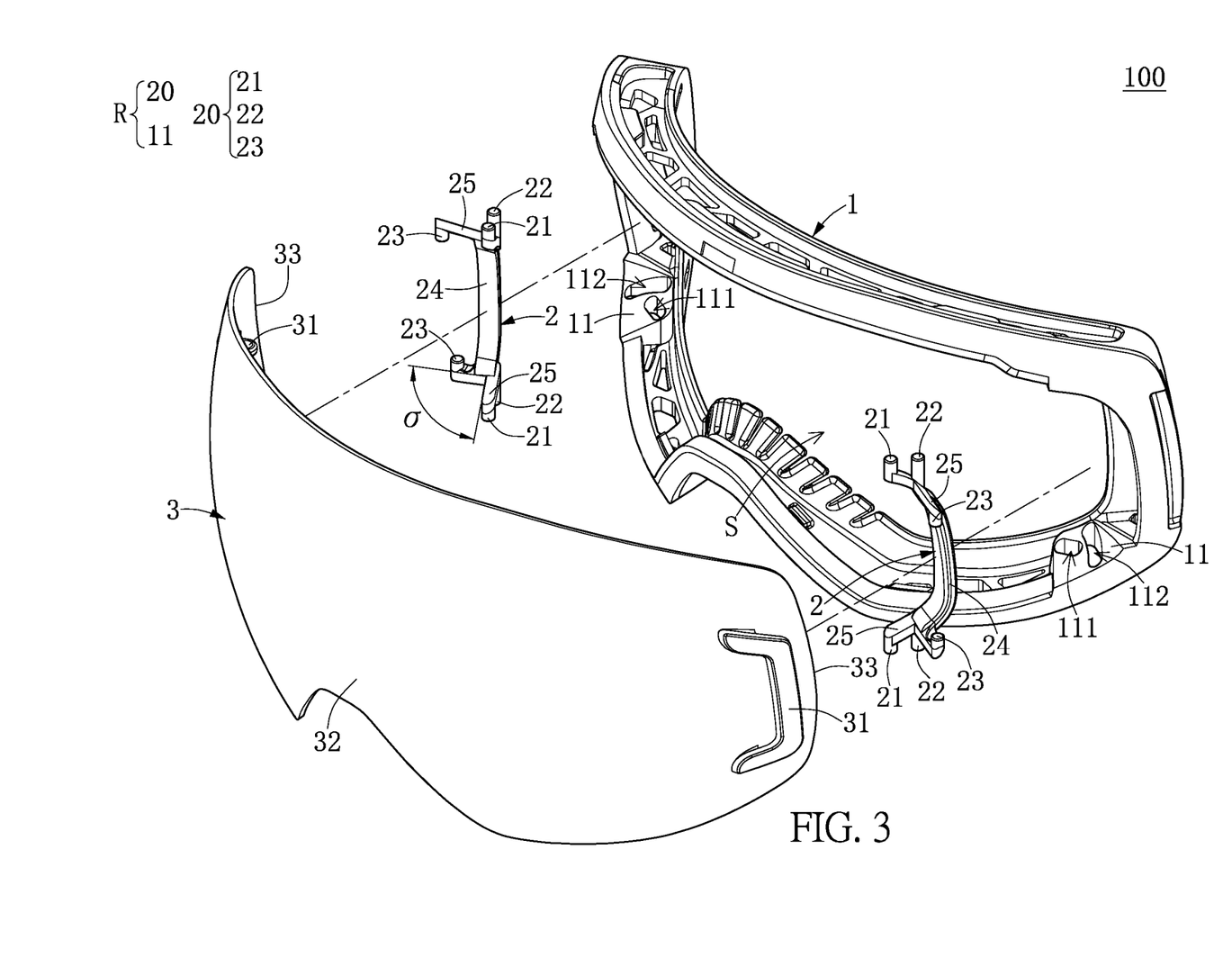
FIG. 3 is another exploded view of FIG. 1.
Figure 4:
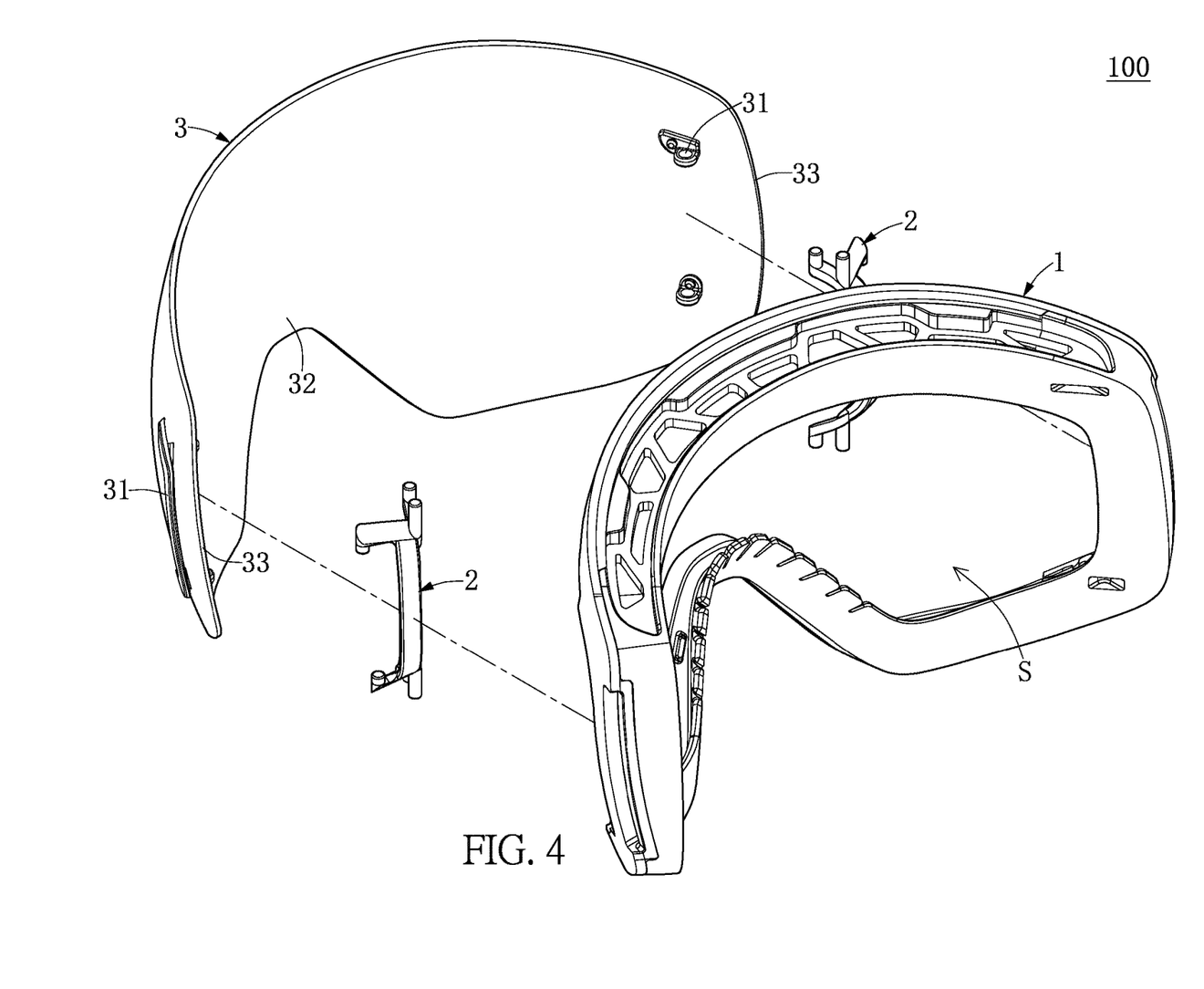
FIG. 4 is an exploded view showing the snow goggle device from another angle of view.
Figure 5:
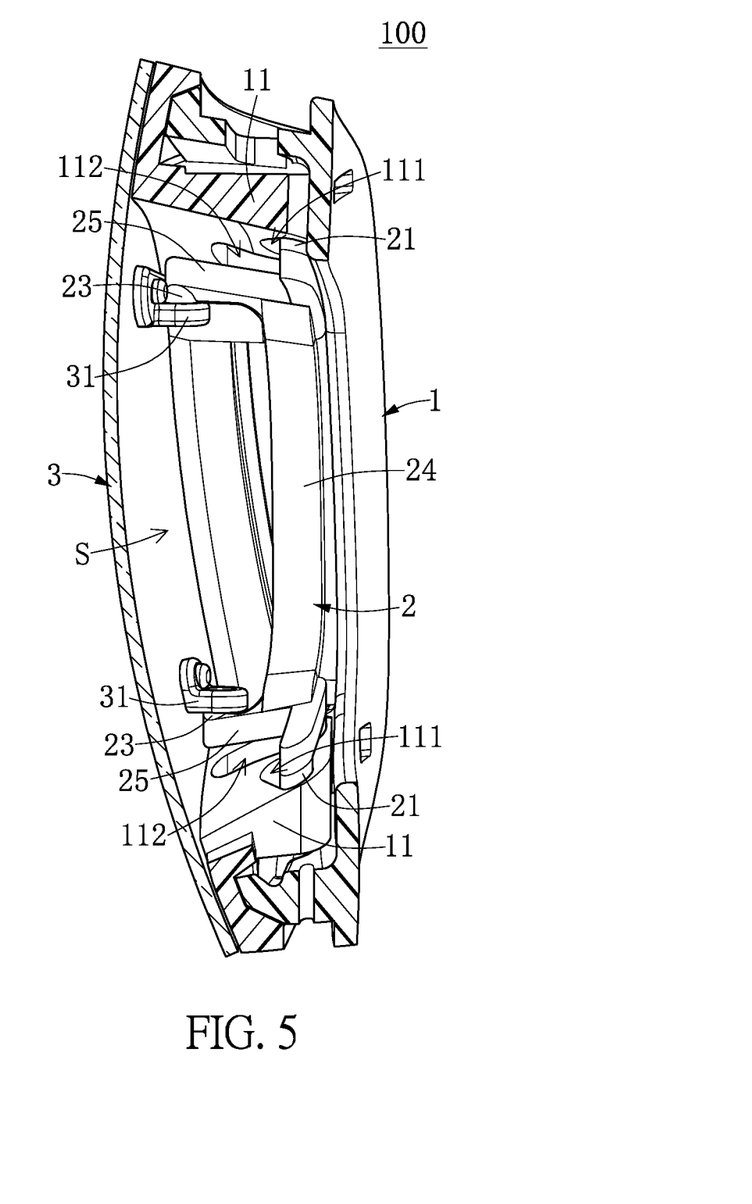
FIG. 5 is a cross-sectional perspective view of the snow goggle device.

As shown in FIG. 3 to FIG. 5, the spectacle frame 1 surroundingly defines an accommodating space S, and the spectacle frame 1 includes two carrying portions 11 arranged at two opposite sides of the accommodating space S (e.g., arranged on the left side and the right side of the spectacle frame 1 shown in FIG. 3). An upper portion and a lower portion of each of the two carrying portions 11 each can be formed with a straight groove 111 and an arced groove 112 shaped related to the straight groove 111. It should be noted that the spectacle frame 1 in the present embodiment is formed by a plurality of components assembled together, but the present disclosure is not limited thereto. For example, in other embodiments which are not described in the present disclosure, the spectacle frame 1 can be a single component.

Specifically, in the straight groove 111 and the arced groove 112 that is cooperated with or arranged adjacent to the straight groove 111, the straight groove 111 is arranged inside a sector area defined by the arced groove 112, and a length of the straight groove 111 is less than that of the arced groove 112 and is less than a radius of curvature of the arced path 112. Moreover, an end of the straight groove 111 (e.g., the left end of the straight groove 111 shown in FIG. 11) arranged adjacent to the arced groove 112 is located in a triangular area defined by the other end of the straight groove 111 (e.g., the right end of the straight groove 111 shown in FIG. 11) and two ends of the arced groove 112.

The two pivoting members 2 are respectively and movably connected to the two carrying portions 11 of the spectacle frame 1, and are substantially in a mirror symmetrical arrangement. Each of the two pivoting members 2 in the present embodiment is integrally formed as a one-piece structure, but the present disclosure is not limited thereto. For example, in other embodiments which are not described in the present disclosure, the pivoting member 2 can be formed by a plurality of components assembled together.

As the two pivoting members 2 are of the same structure, this paragraph discloses the structure of just one of the two pivoting members 2 and the corresponding carrying portion 11 for the sake of brevity. Specifically, the pivoting member 2 includes a supporting shaft 24, two L-shaped frames 25 respectively connected to two ends of the supporting shaft 24, two first pivots 21 respectively connected to the two L-shaped frames 25, two second pivots 22 respectively connected to the two L-shaped frames 25, and two third pivots 23 respectively connected to of the two L-shaped frames 25. For one of the two L-shaped frames 25, the first pivot 21 is connected to an end of the L-shaped frame 25, the second pivot 22 is connected to a corner of the L-shaped frame 25, and the third pivot 23 is connected to the other end of the L-shaped frame 25. The two ends of the supporting shaft 24 are respectively connected to portions of the corners of the two L-shaped frames 25 facing each other, and the two second pivots 22 are respectively connected to portions of the corners of the two L-shaped frames 25 away from each other. The first pivots 21 are respectively connected to portions of the two L-shaped frames 25 away from each other, and the third pivots 23 are respectively connected to portions of the two L-shaped frames 25 facing each other.

Figure 6:
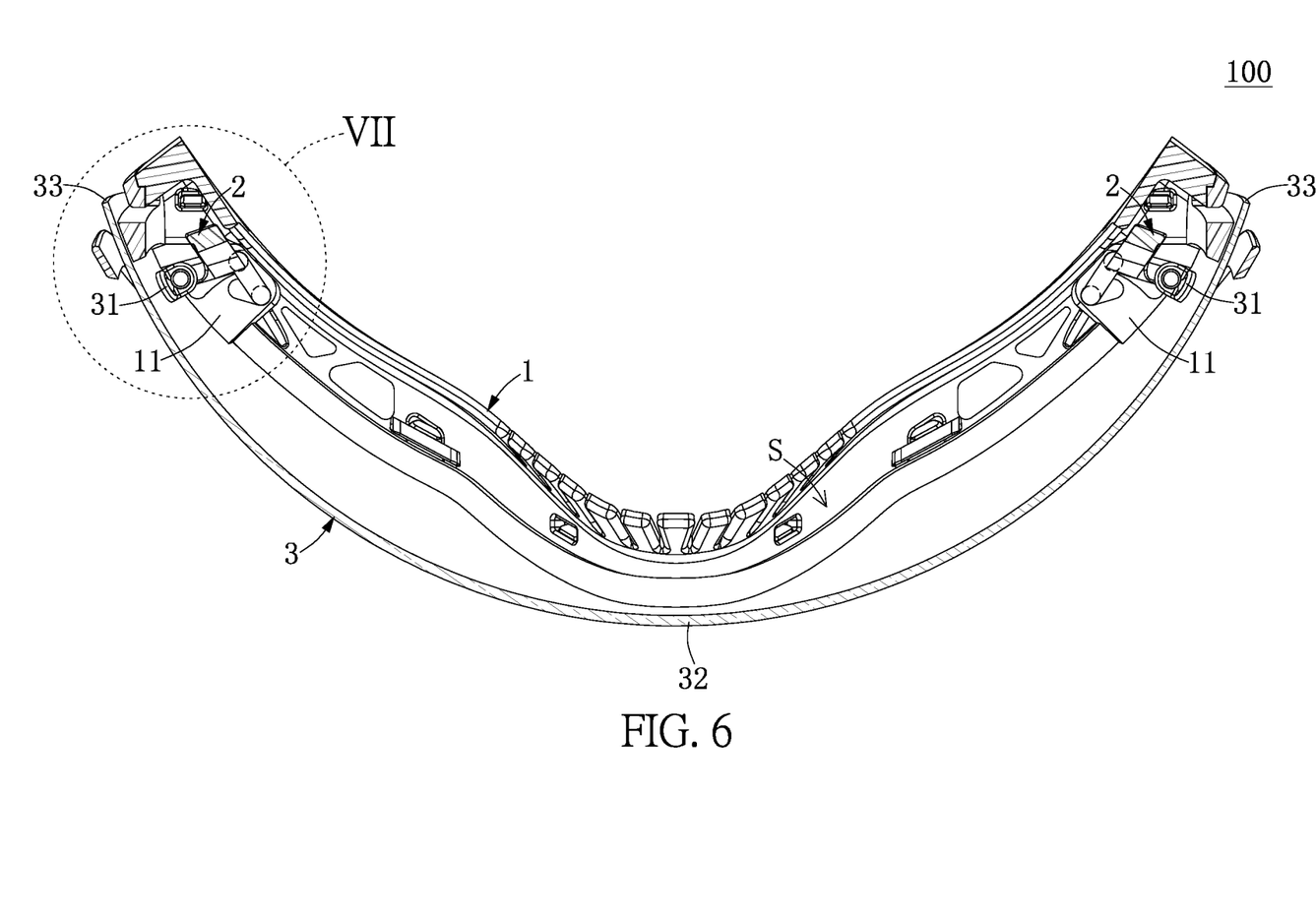
FIG. 6 is a cross-sectional view taken along line VI-VI of FIG. 1.
Figure 7:
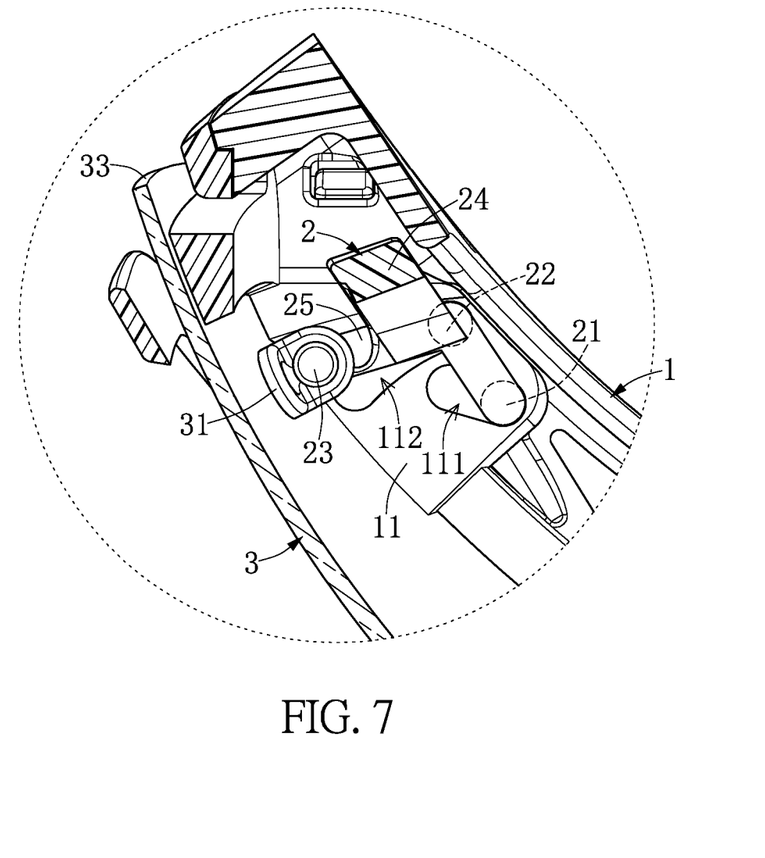
FIG. 7 is an enlarged view of portion V II of FIG. 6.

In each of the two pivoting members 2 and the corresponding carrying portion 11, an inner edge of the corner of any of the two L-shaped frames 25 has an angle σ that is within in a range of 85-105 degrees. As shown in FIG. 5 to FIG. 7, in each of the two pivoting members 2 and the corresponding carrying portion 11, the two first pivots 21 of the pivoting member 2 are movably inserted into the two straight grooves 111 of the carrying portion 11, and the two second pivots 22 of the pivoting member 2 are movably inserted into the two arced grooves 112 of the carrying portion 11.

In addition, the number of each of the L-shaped frames 25, the first pivots 21, the second pivots 22, and the third pivots 23 formed on the pivoting member 2 in the present embodiment is two, but the present disclosure is not limited thereto. For example, in other embodiments which are not described in the present disclosure, the number of each of the L-shaped frame 25, the first pivot 21, the second pivot 22, and the third pivot 23 formed on the pivoting member 2 can be one, and the other components of the snow goggle device 100 can be adjusted according to the structure of the above pivoting member 2.

Figure 8:
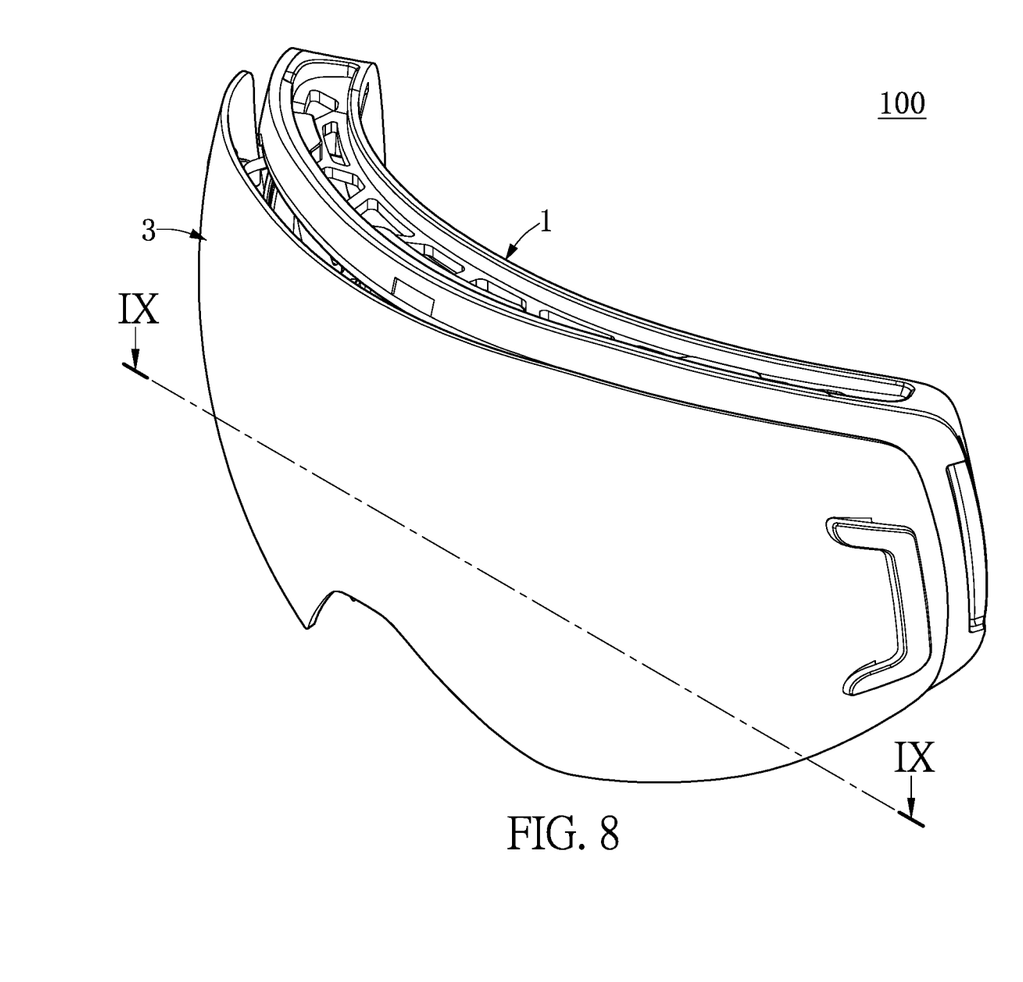
FIG. 8 is a perspective view of the snow goggle device that is at an open position.
Figure 9:
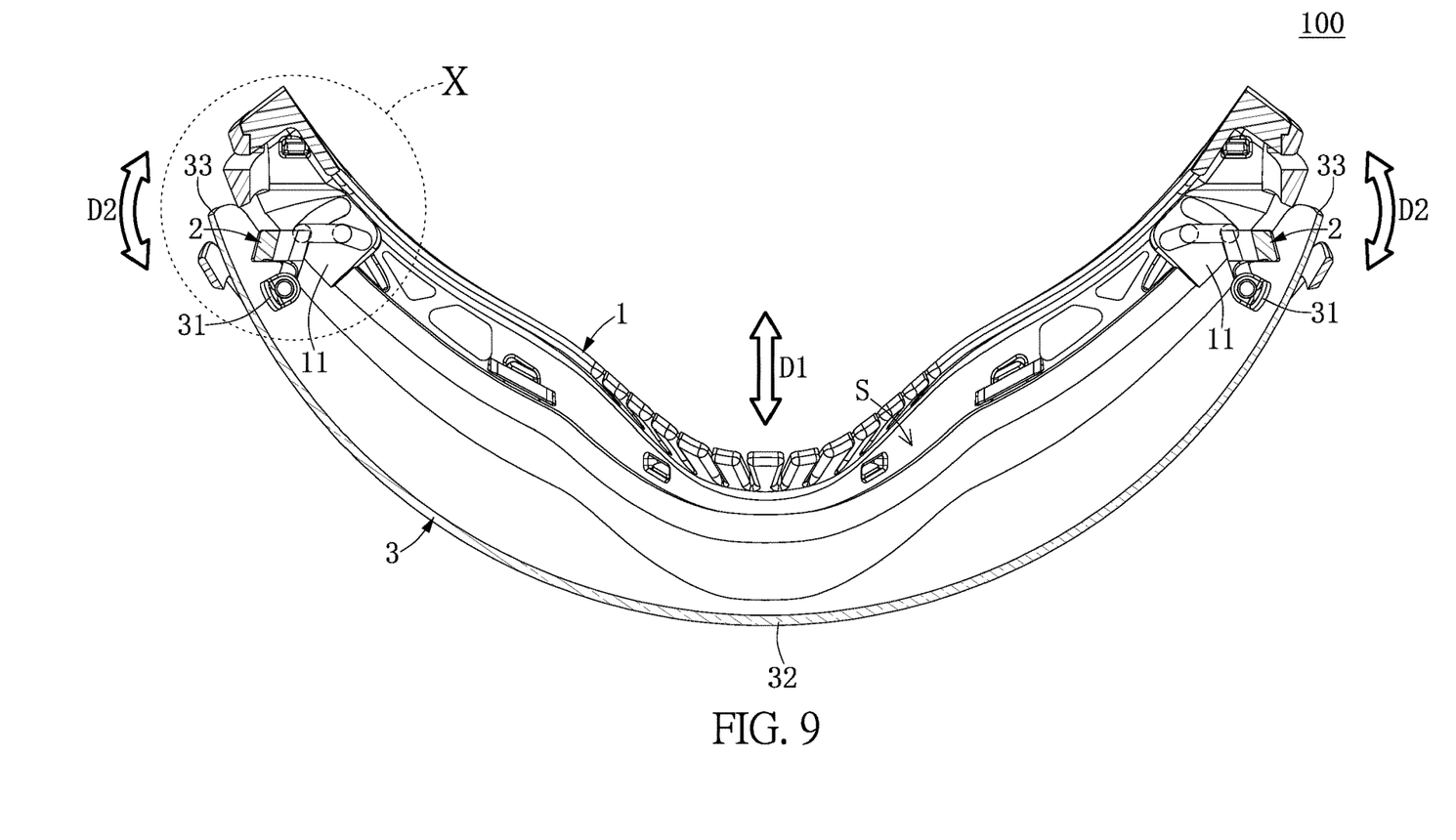
FIG. 9 is a cross-sectional view taken along line IX-IX of FIG. 8.
Figure 10:
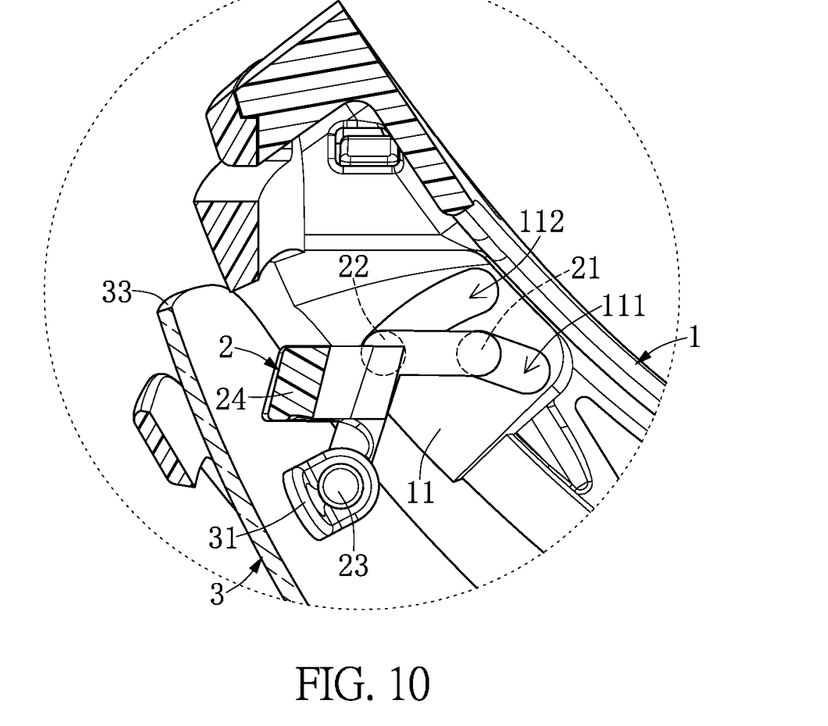
FIG. 10 is an enlarged view of portion X of FIG. 9.

As shown in FIG. 6 and FIG. 7, the curved lens 3 is pivotally connected to the third pivots 23 of the two pivoting members 2. In the present embodiment, the curved lens 3 includes two connecting members 31 arranged on two opposite sides thereof, and the third pivots 23 of the two pivoting members 2 are respectively and pivotally connected to the two connecting members 31 of the curved lens 3, but the present disclosure is not limited thereto. Moreover, the first pivots 21 and the second pivots 22 of each of the two pivoting member 2 can be synchronously moved along the straight grooves 111 and the arced grooves 112, so that the third pivots 23 of the two pivoting members 2 drive the curved lens 3 to move with respect to the spectacle frame 1 between a closed position (as shown in FIG. 1, FIG. 6, and FIG. 7) and an open position (as shown in FIG. 8 to FIG. 10), synchronously causing a deformation of the curved lens 3.

In addition, the structure of the curved lens 3 can be adjusted or changed according to design requirements, and is not limited to the drawings of the present embodiment. For example, in other embodiments which are not described in the present disclosure, the curved lens 3 can be substantially in a spherical shape.

The above description discloses the structure of the snow goggle device 100, and the components of the snow goggle device 100 can be defined as follows in order to further describe the snow goggle device 100 of the present embodiment. As shown in FIG. 2, the first pivot 21, the second pivot 22, and the third pivot 23 connected to the same L-shaped frame 25 are jointly defined as a matching portion 20. In other words, each of the two pivoting members 2 includes two matching portions 20. The matching portions 20 of the two pivoting members 2 are respectively and movably connected to the two carrying portions 11 of the spectacle frame 1, and are substantially in a mirror symmetrical arrangement. In other embodiments not described in the present disclosure, the pivoting member 2 can be formed with one first pivot 21, one second pivot 22, and one third pivot 23. That is to say, the pivoting member 2 can include one matching portion 20.

Figure 11:
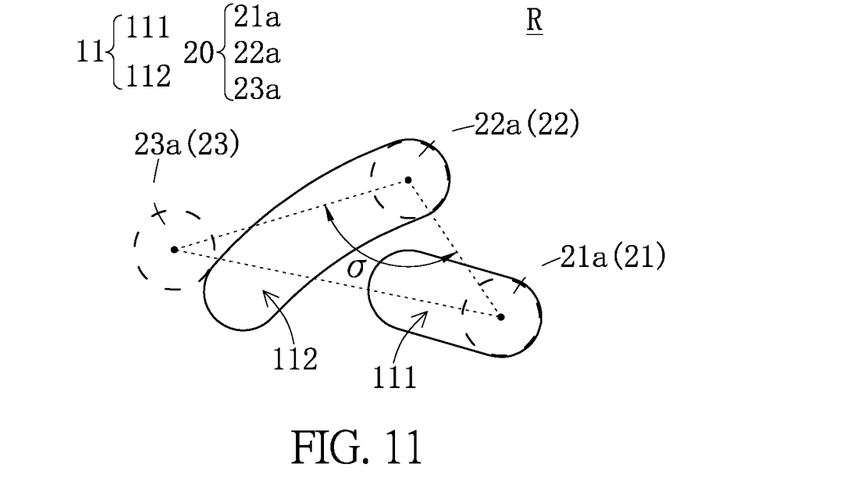
FIG. 11 is a schematic view showing an operation of a pivoting module of the snow goggle device.
Figure 12:
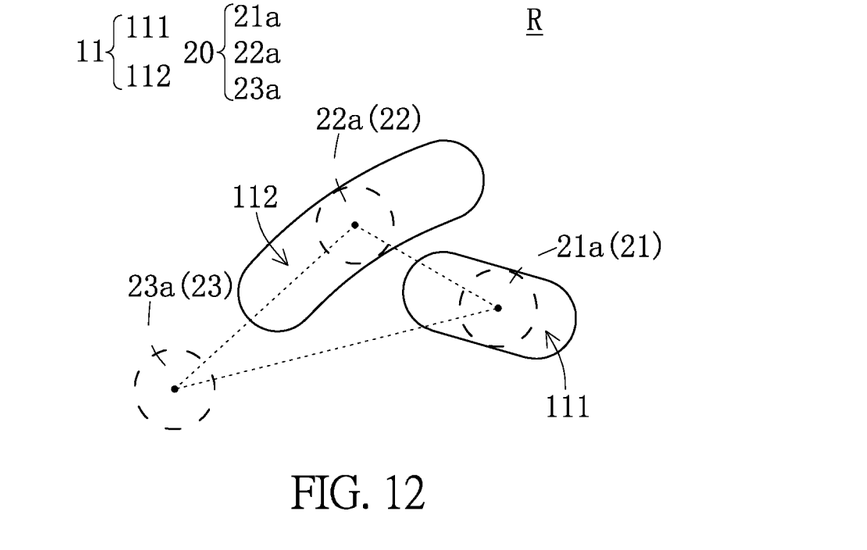
FIG. 12 is a schematic view showing another operation of the pivoting module of the snow goggle device.
Figure 13:
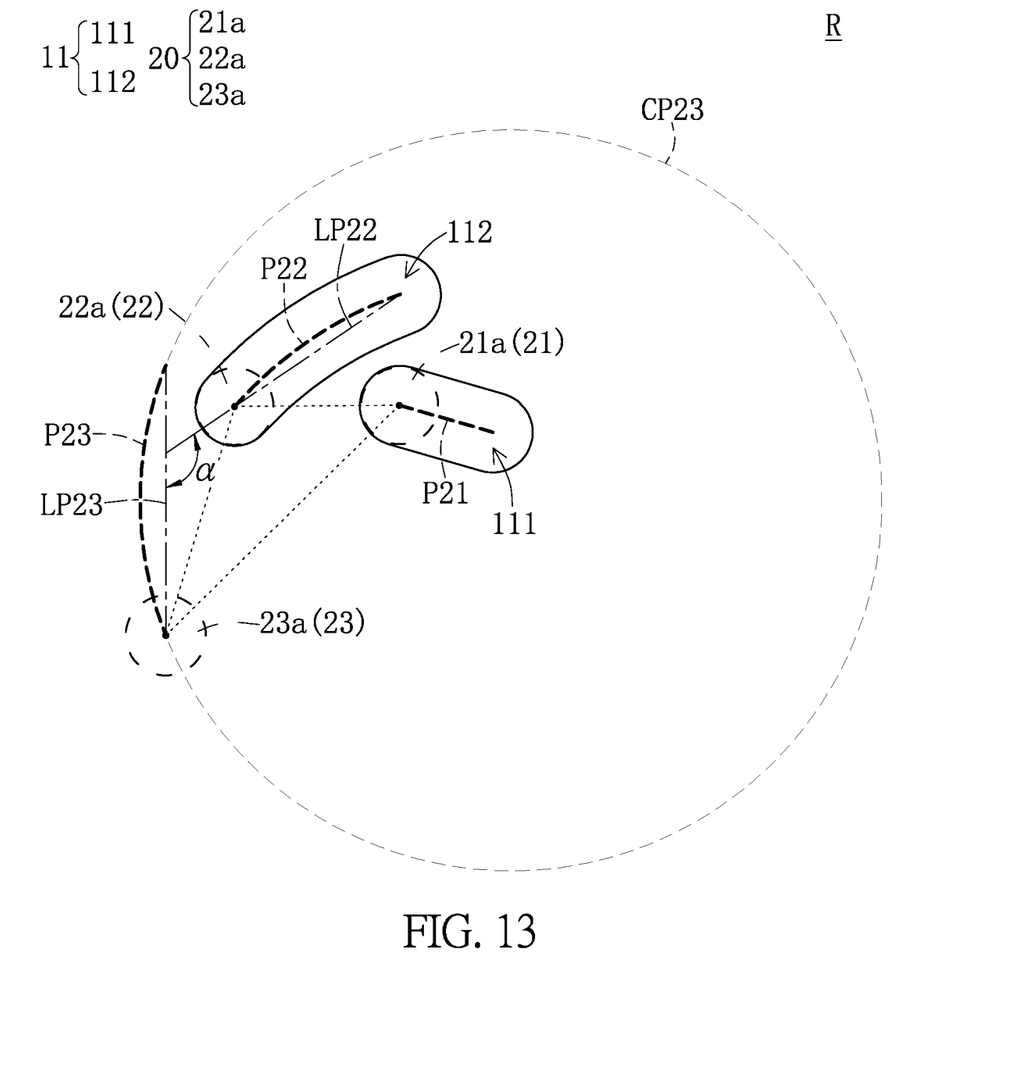
FIG. 13 is a schematic view showing yet another operation of the pivoting module of the snow goggle device.
Figure 14:
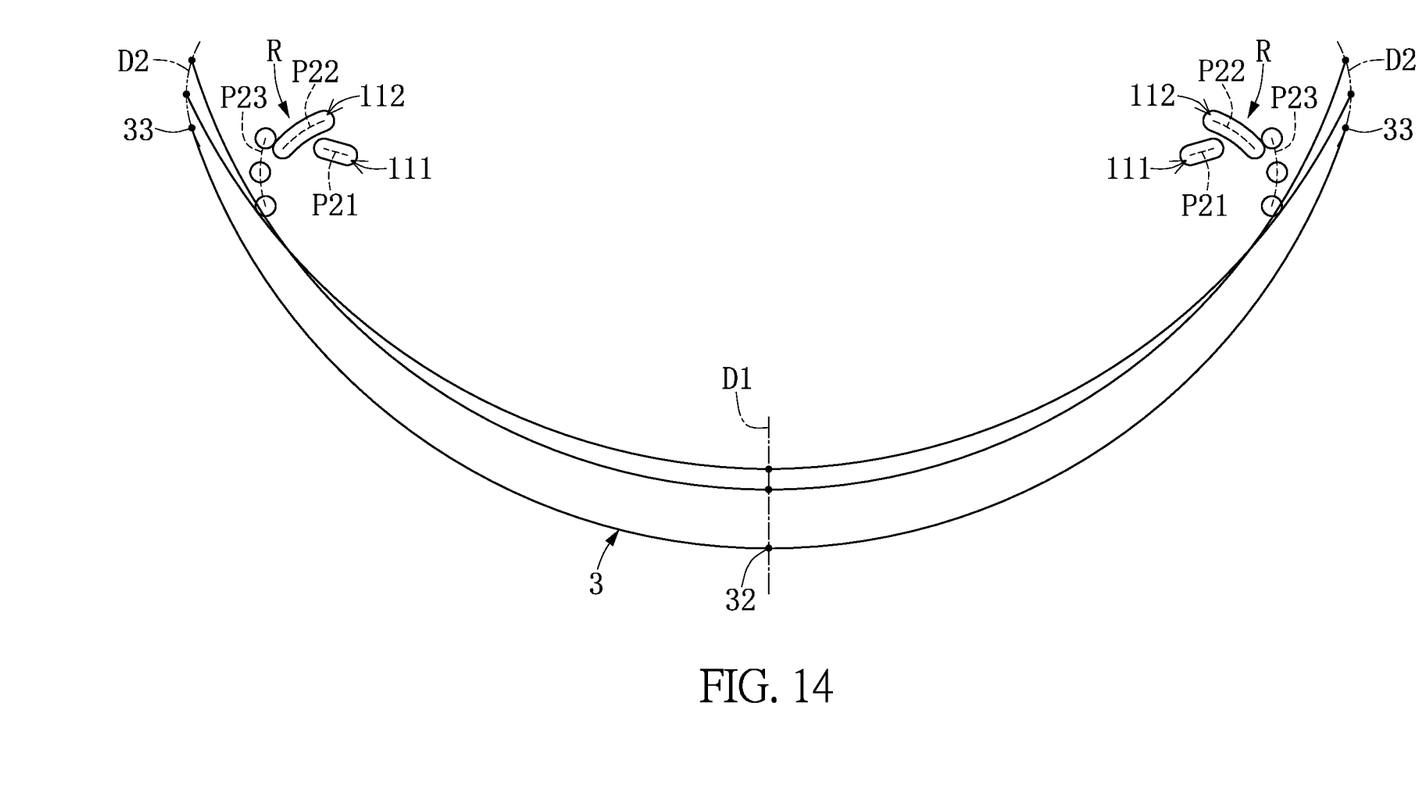
FIG. 14 is a schematic view showing movement of the pivoting module and movement of a curved lens of the snow goggle device.

Moreover, each of the matching portions 20 and the corresponding carrying portion 11 are co-defined as a pivoting module R. In each of the pivoting modules R (as shown in FIG. 11 to FIG. 13), the matching portion 20 is cooperated with the carrying portion 11 to form with a first segment 21a movable along a straight path P21 and a second segment 22a movable along an arced path P22 that is located in an extension direction of the straight path P21. The matching portion 20 of each of the pivoting modules R includes a third segment 23a that is movable along a circular path P23 and that is synchronously movable with the first segment 21a and the second segment 22a.

In the present embodiment, the first segment 21a is identical to the first pivot 21, and the straight path P21 is identical to a moving path of the first pivot 21 along the straight groove 111; the second segment 22a is identical to the second pivot 22, and the arced path P22 is identical to a moving path of the second pivot 22 along the arced groove 112; and the third segment 23a is identical to the third pivot 23, and the circular path P23 is identical to a moving path of the third pivot 23 that is defined by using the movement of the first pivot 21 and the second pivot 22 to synchronously move the third pivot 23, but the present disclosure is not limited thereto. Accordingly, an angle σ defined by the second segment 22a with respect to the first segment 21a and the third segment 23a is within a range of 85-105 degrees, and is identical to the angle σ of the inner edge of the corner defined by the L-shaped frame 25.

In addition, in other embodiments not described in the present disclosure, the first segment 21a, the second segment 22a, and the third segment 23a each can be a slot-like structure, and a corresponding part of the carrying portion 11 can be a pivot-like structure.

As the pivoting modules R are of the same structure, this following description discloses the structure of just one of the pivoting modules R for the sake of brevity. Moreover, each of FIG. 11 to FIG. 14 in the present embodiment is a planar schematic view for clearly showing the configuration and operation of the pivoting module R.

The straight path P21 is arranged inside a sector area defined by the arced path P22. A length of the straight path P21 is less than that of the arced path P22, and is less than a radius of curvature of the arced path P22. In the present embodiment, the radius of curvature of the arced path P22 is preferably within a range of 15-47 cm, and a central angle of the arced path P22 is within a range of 10-30 degrees, but the present disclosure is not limited thereto.

Specifically, an end point of the straight path P21 (e.g., the left end point of the straight path P21 shown in FIG. 11) arranged adjacent to the arced path P22 is located in a triangular area defined by the other end point of the straight path P21 (e.g., the right end point of the straight path P21 shown in FIG. 11) and two end points of the arced path P22. In other words, the end point of the straight path P21 adjacent to the arced path P22 can be located on edges of the triangular area or can be located inside the triangular area.

Moreover, a connecting line LP23 defined by two end points of the circular path P23 and a connecting line LP22 defined by the two end points of the arced path P22 have an angle α that is within a range of 110-130 degrees. The angle α in the present embodiment is 120 degrees, but the present disclosure is not limited thereto.

In addition, a radius of the circular path P23 is less than the radius of curvature of the arced path P22, and the circular path P23 defines a circle area CP23. The straight path P21 and the arced path P22 are arranged in a ½ portion of the circle area CP23, and are preferably arranged in a ⅓ portion of the circle area CP23. In the present embodiment, the radius of the circular path P23 is preferably within a range of 7-20 cm, and a central angle of the circular path P23 is within a range of 20-60 degrees, but the present disclosure is not limited thereto.

As shown in FIG. 11 to FIG. 14, the curved lens 3 is pivotally connected to the third segment 23a of each of the pivoting modules R. When the first segment 21a and the second segment 22a of each of the pivoting modules R are synchronously moved, the third segments 23a of the pivoting modules R drive the curved lens 3 to move with respect to the spectacle frame 1 between the closed position (e.g., the upper curved lens 3 shown in FIG. 14) and the open position (e.g., the lower curved lens 3 shown in FIG. 14), synchronously causing a deformation of the curved lens 3.

Specifically, when the curved lens 3 is at the closed position, the curved lens 3 is disposed on the spectacle frame 1 to enclose one side of the accommodating space S (as shown in FIG. 6) and receives a first stress. The first stress in the present embodiment is more than zero so as to allow the curved lens 3 to abut against the spectacle frame 1, thereby establishing a gapless connection between the curved lens 3 and the spectacle frame 1.

When the curved lens 3 is at the open position, the curved lens 3 is spaced apart from the spectacle frame 1 (as shown in FIG. 9) and receives a second stress. The second stress in the present embodiment is more than zero so as to firmly maintain the relative position between the curved lens 3 and the spectacle frame 1, thereby preventing the curved lens 3 from shaking.

When the curved lens 3 is moved between the closed position and the open position (e.g., the middle of the curved lens 3 shown in FIG. 14), the curved lens 3 receives a third stress that is generated from the deformation and that is larger than each of the first stress and the second stress. The third stress in the present embodiment is a gradually changing value, but the present disclosure is not limited thereto. Specifically, when the curved lens 3 is moved from the closed position to a middle position that is between the closed position and the open position, the third stress will gradually increase from the first stress. When the curved lens 3 is moved from the middle position to the open position, the third stress will gradually decrease to the second stress.

In other words, when the curved lens 3 is moved between the closed position and the open position, a middle portion 32 of the curved lens 3 is moved along a straight direction D1, and two lateral edges 33 of the curved lens 3 opposite to each other are each moved along an arced direction D2 that is substantially parallel to the circular path P23. Accordingly, since each of the two lateral edges 33 of the curved lens 3 is moved along the arced direction D2, the curved lens 3 is deformed and receives the third stress, thereby providing a feeling of operation to a user.

Specifically, when the snow goggle device 100 is in practical use, an user needs to exert an external force to move the curved lens 3 from the closed position to the middle position, in which the curved lens 3 can store an elastic force by the deformation of the curved lens 3, and the curved lens 3 can then be moved from the middle position to the open position merely by slightly pushing the curved lens 3 to release the elastic force.

In addition, the connecting line LP23 defined by the two end points of the circular path P23 in the present embodiment is substantially parallel to the straight direction D1, but the present disclosure is not limited thereto. For example, in other embodiments not described in the present disclosure, the connecting line LP23 and the straight direction D1 can have an angle there-between that is within a range of 5-20 degrees.

In conclusion, in the snow goggle device of the present disclosure, the structural cooperation between the spectacle frame and each of the pivoting members (e.g., the first segment and the second segment of each of the pivoting members are moved along the straight path and the curved path) can be provided to enlarge a radius of a moving path that is related to part of the curved lens pivotally connected to the third segment of the pivoting member, so that the deformation of the curved lens can be effectively reduced.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A snow goggle device, comprising:
a spectacle frame surroundingly defining an accommodating space, wherein the spectacle frame includes two carrying portions, and wherein one of the two carrying portions of the spectacle is arranged at one of two opposite sides of the accommodating space, and another one of the two carrying portions of the spectacle is arranged at another one of the two opposite sides of the accommodating space;
two pivoting members each having a matching portion, wherein the two matching portions are respectively and movably connected to the two carrying portions, and are substantially in a mirror symmetrical arrangement; each of the two matching portions and the corresponding carrying portion are co-defined as a pivoting module; in each of the two pivoting modules, the matching portion is cooperated with the carrying portion to form with a first segment movable along a straight path and a second segment movable along an arced path, and the matching portion includes a third segment synchronously movable with the first segment and the second segment; and the arced path is located in an extension direction of the straight path; and
a curved lens pivotally connected to the third segment of each of the two pivoting modules, wherein when the first segment and the second segment of each of the two pivoting modules are synchronously moved, the third segments of the two pivoting members drive the curved lens to move with respect to the spectacle frame between a closed position and an open position, synchronously causing a deformation of the curved lens,
wherein when the curved lens is at the closed position, the curved lens is disposed on the spectacle frame to enclose one side of the accommodating space and receives a first stress; when the curved lens is at the open position, the curved lens is spaced apart from the spectacle frame and receives a second stress; and when the curved lens is moved between the closed position and the open position, the curved lens receives a third stress that is generated from the deformation and that is larger than each of the first stress and the second stress,
wherein in each of the two pivoting modules, the third segment is movable along a circular path, and a connecting line defined by two end points of the circular path and a connecting line defined by two end points of the arced path have an angle that is within a range of 110-130 degrees,
wherein in each of the two pivoting modules, a radius of the circular path is less than a radius of a curvature of the arced path, the circular path defines a circle area, and the straight path and the arced path are arranged in a ½ portion of the circle area.

2. The snow goggle device according to claim 1, wherein when the curved lens is moved between the closed position and the open position, a middle portion of the curved lens is moved along a straight direction, and two lateral edges of the curved lens opposite to each other each are moved along an arced direction.

3. The snow goggle device according to claim 1, wherein in each of the two pivoting modules, the straight path is arranged inside a sector area defined by the arced path, and a length of the straight path is less than that of the arced path, and is less than the radius of the curvature of the arced path.

4. The snow goggle device according to claim 1, wherein in each of the two pivoting modules, an end point of the straight path arranged adjacent to the arced path is located in a triangular area defined by the other end point of the straight path and two end points of the arced path.

5. The snow goggle device according to claim 1, wherein in each of the two pivoting modules, an angle defined by the second segment with respect to the first segment and the third segment is within a range of 85-105 degrees.

6. A snow goggle device, comprising:
a spectacle frame surroundingly defining an accommodating space, wherein the spectacle frame includes two carrying portions, and wherein one of the two carrying portions of the spectacle is arranged at one of two opposite sides of the accommodating space, and another one of the two carrying portions of the spectacle is arranged at another one of the two opposite sides of the accommodating space;
two pivoting members each having a matching portion, wherein the two matching portions are respectively and movably connected to the two carrying portions, and are substantially in a mirror symmetrical arrangement; each of the two matching portions and the corresponding carrying portion are co-defined as a pivoting module; in each of the two pivoting modules, the matching portion is cooperated with the carrying portion to form with a first segment movable along a straight path and a second segment movable along an arced path, and the matching portion includes a third segment synchronously movable with the first segment and the second segment; and the arced path is located in an extension direction of the straight path; and
a curved lens pivotally connected to the third segment of each of the two pivoting modules, wherein when the first segment and the second segment of each of the two pivoting modules are synchronously moved, the third segments of the two pivoting members drive the curved lens to move with respect to the spectacle frame between a closed position and an open position, synchronously causing a deformation of the curved lens,
wherein when the curved lens is at the closed position, the curved lens is disposed on the spectacle frame to enclose one side of the accommodating space and receives a first stress; when the curved lens is at the open position, the curved lens is spaced apart from the spectacle frame and receives a second stress; and when the curved lens is moved between the closed position and the open position, the curved lens receives a third stress that is generated from the deformation and that is larger than each of the first stress and the second stress,
wherein in each of the two pivoting modules, the third segment is movable along a circular path, and a connecting line defined by two end points of the circular path and a connecting line defined by two end points of the arced path have an angle that is within a range of 110-130 degrees,
wherein in each of the two pivoting modules, a radius of the circular path is less than a radius of curvature of the arced path, the circular path defines a circle area, and the straight path and the arced path are arranged in a ⅓ portion of the circle area.

7. The snow goggle device according to claim 6, wherein when the curved lens is moved between the closed position and the open position, a middle portion of the curved lens is moved along a straight direction, and two lateral edges of the curved lens opposite to each other each are moved along an arced direction.

8. The snow goggle device according to claim 6, wherein in each of the two pivoting modules, the straight path is arranged inside a sector area defined by the arced path, and a length of the straight path is less than that of the arced path, and is less than a radius of curvature of the arced path.

9. The snow goggle device according to claim 6, wherein in each of the two pivoting modules, an end point of the straight path arranged adjacent to the arced path is located in a triangular area defined by the other end point of the straight path and two end points of the arced path.

10. The snow goggle device according to claim 6, wherein in each of the two pivoting modules, an angle defined by the second segment with respect to the first segment and the third segment is within a range of 85-105 degrees.

* * * * *